(12) United States Patent
Miller

(10) Patent No.: US 8,556,564 B2
(45) Date of Patent: Oct. 15, 2013

(54) MOBILE SAMPLE STORAGE AND RETRIEVAL UNIT FOR A LABORATORY AUTOMATED SAMPLE HANDLING WORKSYSTEM

(75) Inventor: Kerry L. Miller, Elkton, MD (US)

(73) Assignee: Siemens Healthcare Diagnostics Inc., Deerfield, IL (US)

(*) Notice: Subject to any disclaimer, the term of this patent is extended or adjusted under 35 U.S.C. 154(b) by 1094 days.

(21) Appl. No.: 11/768,525

(22) Filed: Jun. 26, 2007

(65) Prior Publication Data
US 2009/0003981 A1 Jan. 1, 2009

(51) Int. Cl.
*B65G 1/00* (2006.01)

(52) U.S. Cl.
USPC ...................................... 414/331.11; 414/277

(58) Field of Classification Search
USPC ............... 414/287, 266, 267, 331.18, 331.06, 414/331.1, 331.15, 331.17, 331.09, 331.05, 414/331.01, 331.02, 331.14, 217, 281, 277, 414/331.11; 454/193; 62/440
See application file for complete search history.

(56) References Cited

U.S. PATENT DOCUMENTS

| | | | |
|---|---|---|---|
| 3,743,116 A * | 7/1973 | Giessler et al. | 414/279 |
| 3,792,785 A * | 2/1974 | Weir | 414/278 |
| 3,984,012 A * | 10/1976 | Ennis et al. | 414/231 |
| 4,049,123 A * | 9/1977 | Fegley et al. | 209/555 |
| 4,059,194 A * | 11/1977 | Barry | 414/278 |
| 4,108,333 A * | 8/1978 | Falk et al. | 221/13 |
| 4,195,962 A * | 4/1980 | Laskowski et al. | 414/659 |
| 4,720,463 A | 1/1988 | Farber et al. | |
| 4,959,020 A | 9/1990 | Di Rosa | |
| 4,981,409 A * | 1/1991 | Hirose et al. | 414/223.01 |
| 4,986,715 A * | 1/1991 | Asakawa | 414/331.05 |
| 4,987,765 A * | 1/1991 | Nishimura et al. | 72/405.03 |
| 5,110,248 A * | 5/1992 | Asano et al. | 414/172 |
| 5,570,990 A | 11/1996 | Bonora et al. | |
| 5,622,470 A * | 4/1997 | Schaefer et al. | 414/807 |
| 5,664,928 A * | 9/1997 | Stauber | 414/269 |
| 5,810,061 A * | 9/1998 | Yuyama | 141/129 |
| 5,810,062 A * | 9/1998 | Bonora et al. | 141/351 |
| 6,047,855 A * | 4/2000 | Lin | 221/150 HC |
| 6,113,336 A * | 9/2000 | Chang et al. | 414/281 |
| 6,129,428 A * | 10/2000 | Helwig et al. | 312/114 |
| 6,143,040 A * | 11/2000 | Tometsuka et al. | 29/25.01 |
| 6,513,282 B2 | 2/2003 | Schott et al. | |
| 6,581,395 B2 * | 6/2003 | Felder et al. | 62/177 |
| 6,629,812 B1 * | 10/2003 | Lee et al. | 414/788.8 |
| 6,721,615 B2 | 4/2004 | Fava et al. | |

(Continued)

FOREIGN PATENT DOCUMENTS

| | | |
|---|---|---|
| JP | H2-024459 A | 1/1990 |
| JP | H6-074958 A | 3/1994 |
| JP | H9-211005 A | 8/1997 |
| JP | 2006-347773 A | 12/2006 |

OTHER PUBLICATIONS

English Abstract of JP H6-074958(A), 2 pages, Mar. 18, 1994.
English Abstract of JP H9-211005(A), 1 page, Aug. 15, 1997.

(Continued)

*Primary Examiner* — James Keenan
*Assistant Examiner* — Glenn Myers
(74) *Attorney, Agent, or Firm* — Leland K. Jordan

(57) ABSTRACT

A mobile, thermally insulated storage and retrieval unit for housing tube racks on shelves and having an elevator and conveyor for moving racks between shelves and an exterior loading tray.

16 Claims, 13 Drawing Sheets

(56) References Cited

U.S. PATENT DOCUMENTS

| | | |
|---|---|---|
| 6,742,344 B2 | 6/2004 | Vormetal |
| 6,974,019 B2 * | 12/2005 | Lapeyre et al. .......... 198/370.02 |
| 7,013,197 B2 | 3/2006 | Melching et al. |
| 2004/0017556 A1 * | 1/2004 | Nakahara ........................ 355/70 |
| 2004/0037679 A1 * | 2/2004 | Sato et al. ..................... 414/281 |
| 2004/0037680 A1 * | 2/2004 | Sato et al. ..................... 414/281 |
| 2004/0149672 A1 * | 8/2004 | Motoori et al. ............... 212/332 |
| 2004/0213651 A1 * | 10/2004 | Malin ...................... 414/331.05 |
| 2006/0099054 A1 * | 5/2006 | Friedman et al. ............. 414/217 |
| 2007/0041814 A1 | 2/2007 | Lowe |

OTHER PUBLICATIONS

English Abstract of JP H2-024459(A), 2 pages, Jan. 26, 1990.
English Abstract of JP 2006-347773(A), 1 page, Dec. 28, 2006.

* cited by examiner

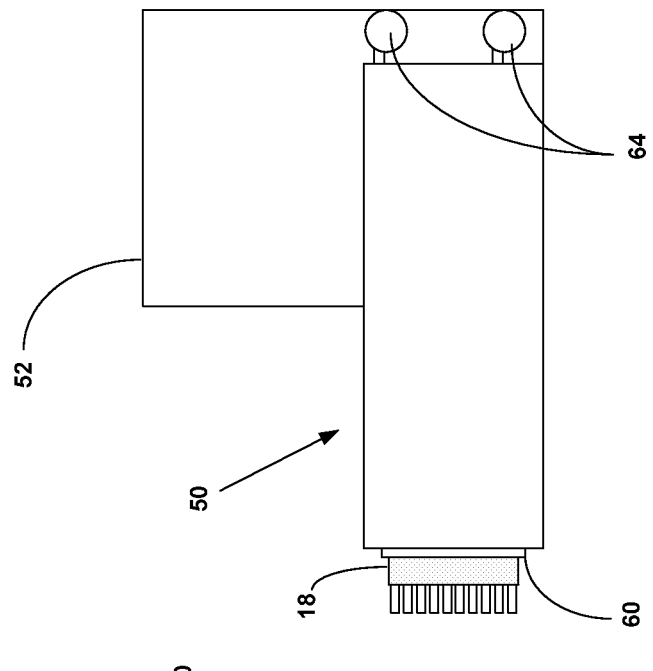
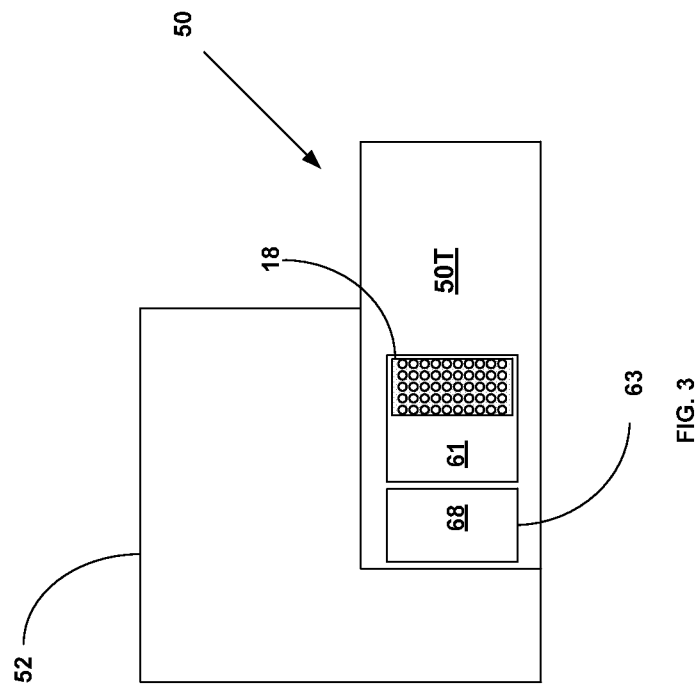

MOBILE SAMPLE STORAGE AND RETRIEVAL UNIT FOR A LABORATORY AUTOMATED SAMPLE HANDLING WORKSYSTEM

FIELD OF THE INVENTION

The present invention relates to an automated clinical sample handling laboratory system with one or more independent processing stations having pre-processed samples supplied thereto by an automated conveyor system. More particularly, the present invention relates to an automated sample storage and retrieval unit for temporarily maintaining samples in a controlled environment.

BACKGROUND OF THE INVENTION

Clinical diagnostic analyzers with increasing levels of complexity and sophistication are being developed to perform chemical assays and immunoassays of biological fluid samples such as urine, blood serum, plasma, cerebrospinal liquids and the like, with much emphasis placed on reducing the time to obtain an initial test result and/or increasing analytical throughput. Throughput improvements, while desirable, may be hampered if corresponding advances are not made in the automation of pre-analytical sample preparation and handling operations like sorting, batch preparation, centrifugation of sample tubes to separate sample constituents, cap removal to facilitate fluid access, and the like.

Laboratory automation systems (LAS) have been developed to handle specimens (blood, urine, and body fluids) contained in standard, bar code-labeled, evacuated tubes. The bar code label contains an accession number coupled to demographic information that is entered into a hospital's Laboratory Information System (LIS) together with test orders and other desired information. An operator places the labeled tubes onto the LAS system which performs all functions automatically including sample sorting, routing, centrifugation, aliquot preparation, sample analysis at one or more analyzers, before making the tested sample available for post-analytical storage and retrieval.

Subsequent to processing, and because as many as one tenth of all processed tubes are required for additional tests or for retesting, patient samples are advantageously stored in refrigerated space and retrieved when follow-on testing is required. Automated, refrigerated storage and retrieval systems are available in either of two basic types. In one instance, the storage and retrieval systems are connected directly to the laboratory work-system and sample tubes are robotically removed from the conveyor and stored in a refrigerated unit placed nearby the LAS. Such LAS-connected storage-and-retrieval systems have disadvantages because the space nearby the work-system is often scarce or has a higher priority demand and because storage therein is limited to samples tested on the connected LAS. For these reasons, storage and retrieval systems are more typically placed in a remote location and sample tubes are placed in racks which are moved by an operator to the remote storage and retrieval system where the racks are robotically stored and retrieved when required. Tubes are typically selected by a robot, inventoried by reading the bar code, and transferred to large-capacity storage trays that are mechanically transferred into refrigerated storage; samples are also automatically discarded upon expiration of their designated storage time. Such storage and retrieval systems generally include conventional industrial inventory management operation having on-board inventory control and tracking software, and an overall system controller.

Laboratory automation systems having pre-processing capabilities are known and these generally include conveyor systems for conveying specimens to analyzers, such as those described in U.S. Pat. Nos. 6,060,022, 6,220,451, and 7,141,213, discussed below. Typical of such systems, a sample is transported to an analyzer by a primary conveyor and either removed from the primary conveyor by a robotic-like device and placed into a sampling area of an adjacent analyzer or may be shuttled onto an analyzer-specific conveyor that transports the sample to the sampling area of an adjacent analyzer. In the later instance, when sufficient sample aliquots have been removed from the sample, the sample is returned to the primary conveyor and transferred thereto from the analyzer-specific conveyor.

U.S. Pat. No. 6,742,344 discloses a shelved cupboard for refrigerated goods, comprising an opening for putting in or removing refrigerated goods and an arrangement of ducts for circulation of cooled air from an associated cooling element, such as an evaporation battery. The air that is circulated in the ducting system and the interior of the cupboard, as well as between the refrigerated goods, may be cooled to a greater or lesser degree by primary or secondary air.

U.S. Pat. No. 7,141,213 discloses a modular workstation that can automatically prepare biological specimens for further processing by a large variety of analytical equipment, without having to replace existing analytical equipment. The system can sort incoming samples, and prioritize STAT samples. As needed, incoming samples can be automatically centrifuged, decapped, and transported to selected analytical equipment. The system can be automatically controlled through the use of a central controller. The system provides efficient, high throughput and fast turnaround analytical results, with decreased chance for operator error and decreased exposure of operators to biological substances.

U.S. Pat. No. 6,060,022, automatically presents pre-processed samples in open containers to robotic devices operated in conjunction with independent stand-alone analyzers. In order to provide precise and accurate handling of the sample tubes, it is critical to position and align the tubes within a sample tube carrier accurately so that the various robotic handling devices may automatically and consistently remove or replace tubes from tube carriers as needed.

Although these prior art systems have advanced sample handling and processing throughput, existing sample storage-and-retrieval systems have the disadvantages of either requiring a large amount of laboratory space or of requiring an operator to transport and retrieve racks to and from a remote location. This is particularly disadvantageous since it has been discovered that a large number of samples required to be re-tested are initially tested on the same day that follow-on tests are ordered.

SUMMARY OF THE INVENTION

The present invention provides a mobile sample storage and retrieval unit that is adapted for automatically maintaining a nominal number of already analyzed samples nearby an LAS for a defined length of time, typically one day, in the event re-testing is required during that same 24-hour period. At the end of the 24-hour period, an operator moves the mobile sample storage and retrieval unit to a much larger, remote refrigerated storage and retrieval systems remote where a significantly larger number of sample tube racks are stored for designated periods of time, possibly being a week or more. The mobile sample storage and retrieval unit of the present invention is equipped with a controller programmed to track the location of each stored sample tube and to automatically retrieve any sample for which re-testing is required. The sample storage and retrieval unit is also adapted to be refrigerated by an external source of conditioned air in order to reduce its weight and complexity.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein:

FIG. 3 is a schematic top plan view of the sample storage and retrieval unit of FIG. 1 docked into a refrigerated air source;

FIG. 4 is a schematic side elevation view of the sample storage and retrieval unit of FIG. 1 docked into a refrigerated air source;

DETAILED DESCRIPTION OF THE PREFERRED EMBODIMENTS

Figure 1:
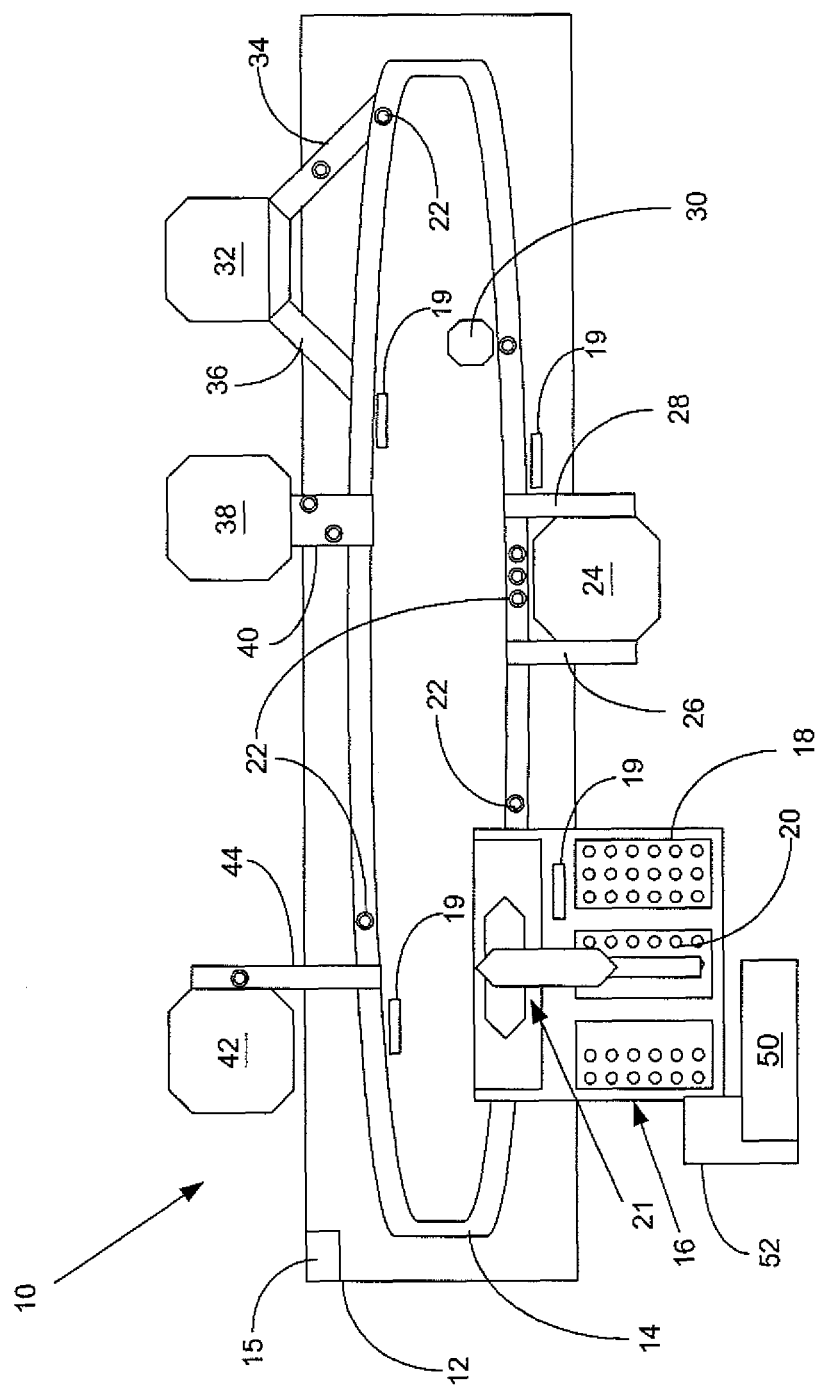
FIG. 1 is a simplified schematic plan view of an automated sample handling system including a conveyor controlled in cooperation with several chemical analysis pre-treatment devices and analyzers in which the present invention may be employed advantageously.

Referring to FIG. 1, there is illustrated a conventional Laboratory Automation System 10 (LAS 10) capable of automatically pre-processing as necessary multiple sample containers 20, typically sample test tubes, contained in multiple tube racks 18. Sample containers 20 may also be adapted to hold reagents, calibration solutions and/or Quality Control materials.

Typically, patient specimens to be automatically processed are provided to sample handling system 10 in multiple containers, such as test tubes, which can be capped. Each of the sample containers 20 is provided with container identification indicia, such as a bar code, indicating a patient's identification, as well as, optionally, the assay procedures to be accomplished upon the sample therein and/or time period for which a sample is to be retained after analysis in the event additional, "follow-on" testing is required. Racks 18 also have identification indicia thereon for purposes of tracking.

LAS 10 comprises an operating base 12 on which a belt-like conveyor track 14 transports a plurality of individual sample tube containers 20 carried in sample tube carriers 22 from a sample tube loading/unloading station 16 to an automated centrifuge 24 to an automated tube de-capper 30 for automatically removing caps from capped sample containers 20 and to one or more conventional clinical analyzers 32, 38, and 42 before returning each sample container 20 to the sample tube loading/unloading robotic station 16. It will be understood that more than three analyzers 32, 38, and 42 may be linked by conveyor track 14, but for purposes of simplicity, only three are shown. LAS 10 has a number of sensors, not illustrated, for detecting the location of a sample tube container 20 by means of identifying indicia placed on or within each sample tube carrier 22. Conventional bar-code readers may be employed in such tracking operations.

Centrifuge 24 and each analyzer 38, 42 and 32 are generally equipped with various robotic mechanisms 26 and 28, 40 and 44 or analyzer tracks 34 and 36, respectively, for removing a sample tube carrier 22 from conveyor track 14, moving the sample tube carrier 22 to and from centrifuge 24, to and from or into and out from analyzers 38, 42 and 32, respectively. Typically, the loading/unloading station 16 includes at least two X-Y-Z robotic arms 21 conventionally equipped with clamping robotic hands.

LAS 10 is controlled by a conventional computer 15 preferably a microprocessor based central processing unit CPU 15 housed as part of or separate from the system 10 to move the sample tube carrier 22 to each operating station 24, 30, 32, 38, 42 and 16 whereat various types of assay processing occurs. CPU 15 controls sample handling system 10 according to software, firmware, or hardware commands or circuits like those used on the Dimension® clinical chemistry analyzer sold by Dade Behring Inc. of Deerfield, Ill., and are typical of those skilled in the art of computer-based electro-mechanical control programming.

Included schematically in FIG. 1 is the mobile sample storage and retrieval unit 50 of the present invention that is adapted for automatically maintaining a number of already analyzed samples nearby LAS 10 for a defined length of time, typically one day, in the event re-testing is required during that same 24-hour period. What has been discovered is that a large number of incidences wherein re-testing of a sample is required occur the same day during which the sample is originally tested. Thus, by properly sizing storage and retrieval unit 50 and maintaining it nearby LAS 10, the efficiency of sample re-testing can be increased. Consequently, mobile storage and retrieval unit 50 is preferably sized to accommodate generally about 1,000 sample tubes 20 contained in generally about twenty or more racks 18. In the event that a laboratory processes much more than generally about 1,000 sample tubes 20 in a 24-hour period, then more than one mobile storage and retrieval unit 50 may be employed. The general objective of the present invention is that the mobile storage and retrieval unit 50 would need to be moved to a conventional much larger remote sample storage and retrieval refrigerator about once daily for purposes of operating efficiency. FIG. 1 schematically illustrates mobile storage and retrieval unit 50 as docked into a stationary refrigeration unit 52 that is conventionally configured to provide a supply of refrigerated air to the interior of mobile storage and retrieval unit 50 so as to maintain sample tubes 20 stored therein within controlled environmental conditions. Storage and retrieval unit 50 is internally insulated and, as described below, is configured so as to be automatically loaded with racks 18 when docked into refrigeration unit 52 proximate LAS 10 and is further adapted so that any one of the racks stored therein can be automatically retrieved from storage in the event a follow-on analysis of a sample is required during the time the sample is stored inside storage and retrieval unit 50. Ideally, sample tube loading/unloading robotic station 16 is adapted to also remove racks 18 from LAS 10 and place them on a loading tray 60 of storage and retrieval unit 50 described hereinafter. As further described hereinafter, in the event re-testing of a sample is required during the aforementioned 24-hour period, sample tube loading/unloading robotic station 16 is operated to remove racks 18 from storage and retrieval unit 50 and re-place them in loading/unloading robotic station 16 from which they may be processed as described above. In order to further increase its utility, storage and retrieval unit 50 is separable from refrigeration unit 52 to increase mobility and decrease weight when storage and retrieval unit 50 is moved from LAS 10 into a remote sample storage refrigerator.

Figure 2:
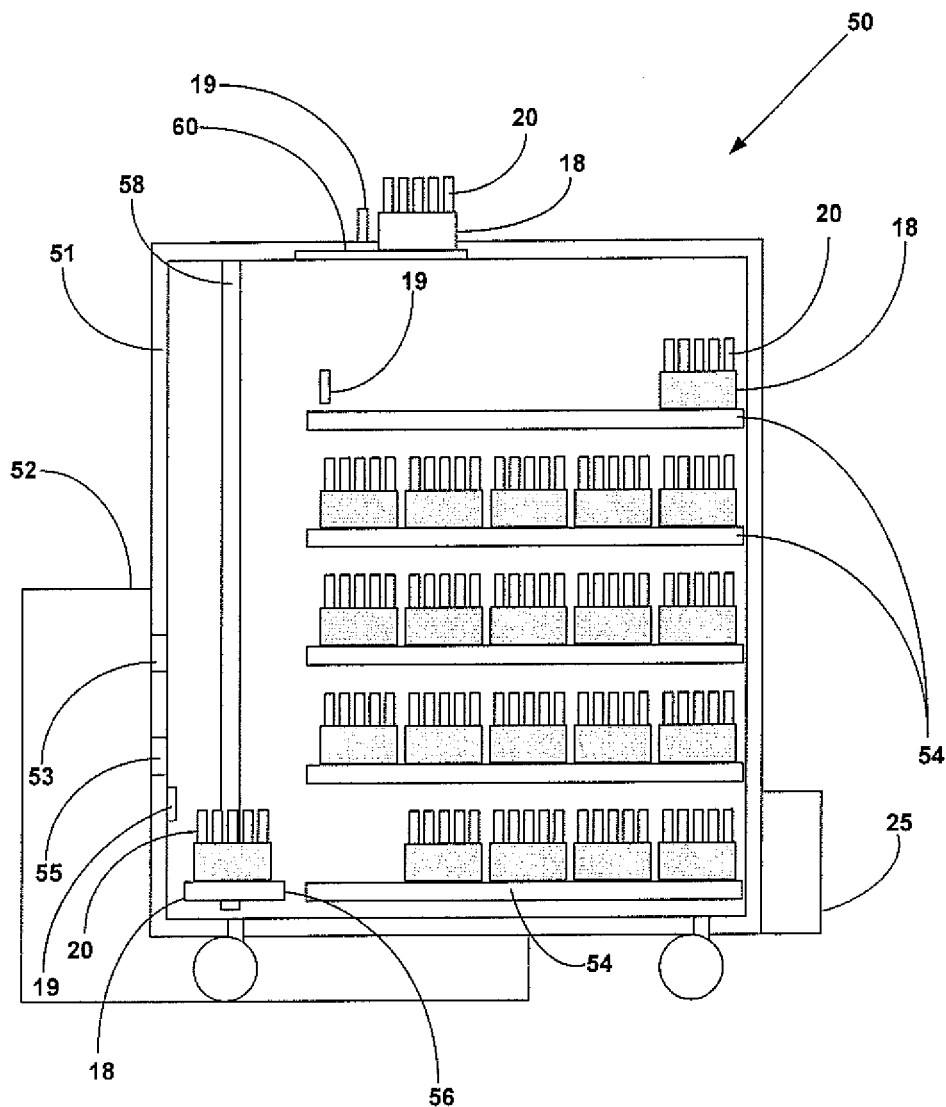
FIG. 2 is a sectional side elevation view of the sample storage and retrieval unit of the present invention.

FIG. 2 is a sectional side elevation view of mobile storage and retrieval unit 50 illustrating a number of horizontal interior shelves 54, each shelf 54 capable of holding a number of racks 18 thereon. Racks 18 may accommodate sample tubes 20. All exterior walls of mobile storage and retrieval unit 50 are insulated with an appropriate layer of thermal blanketing 51; one of the vertical walls is also provided with a refrigerated air inlet duct 53 and an outlet duct 55 for docking with stationary refrigeration unit 52, along the general lines as disclosed in U.S. Pat. No. 6,742,344. An important feature of the present invention is a vertically translatable elevator 56 including a motorized belt or track 58 for vertically moving elevator 56 from a position horizontally aligned with the lowermost shelf 54 to a position horizontally aligned with a loading tray 60 located atop storage and retrieval unit 50.

FIG. 3 is a top view of storage and retrieval unit 50 as docked with refrigeration unit 52 also illustrating an opening 63 at the top of storage and retrieval unit 50 and above elevator 56 so that racks 18 may be passed into and out of storage and retrieval unit 50 onto loading tray 60. Loading tray 60 is equipped with a loading tray conveyor 61 that can be freely driven in both clockwise and counter-clockwise direction in a manner like an elevator belt conveyor 68 and a shelf belt conveyor 70 described hereinafter. FIG. 4 is a side elevation view of storage and retrieval unit 50 as docked with refrigeration unit 52 also illustrating two of four rolling members, shown here as lockable caster wheels 64 that provide mobility to storage and retrieval unit 50 as it is moved from LAS 10 to a remote sample storage refrigerator. Those skilled in the art will recognize that other mechanisms adapted to move the unit, such as track systems, may be used in other embodiments of the invention.

Figure 5:
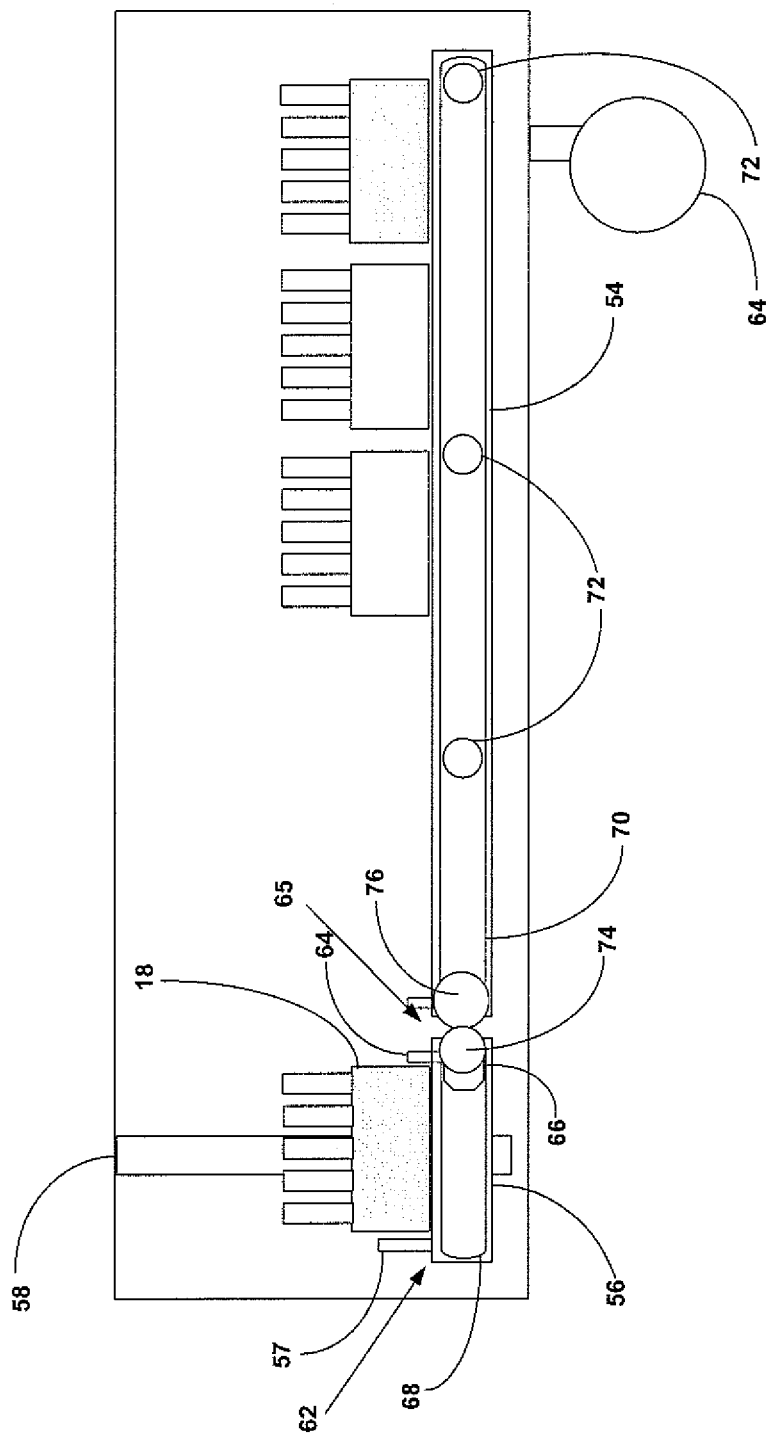
FIG. 5 is an enlarged sectional view of a portion of the sample storage and retrieval unit of FIG. 1 illustrating a vertically translatable elevator therein.
Figure 6:
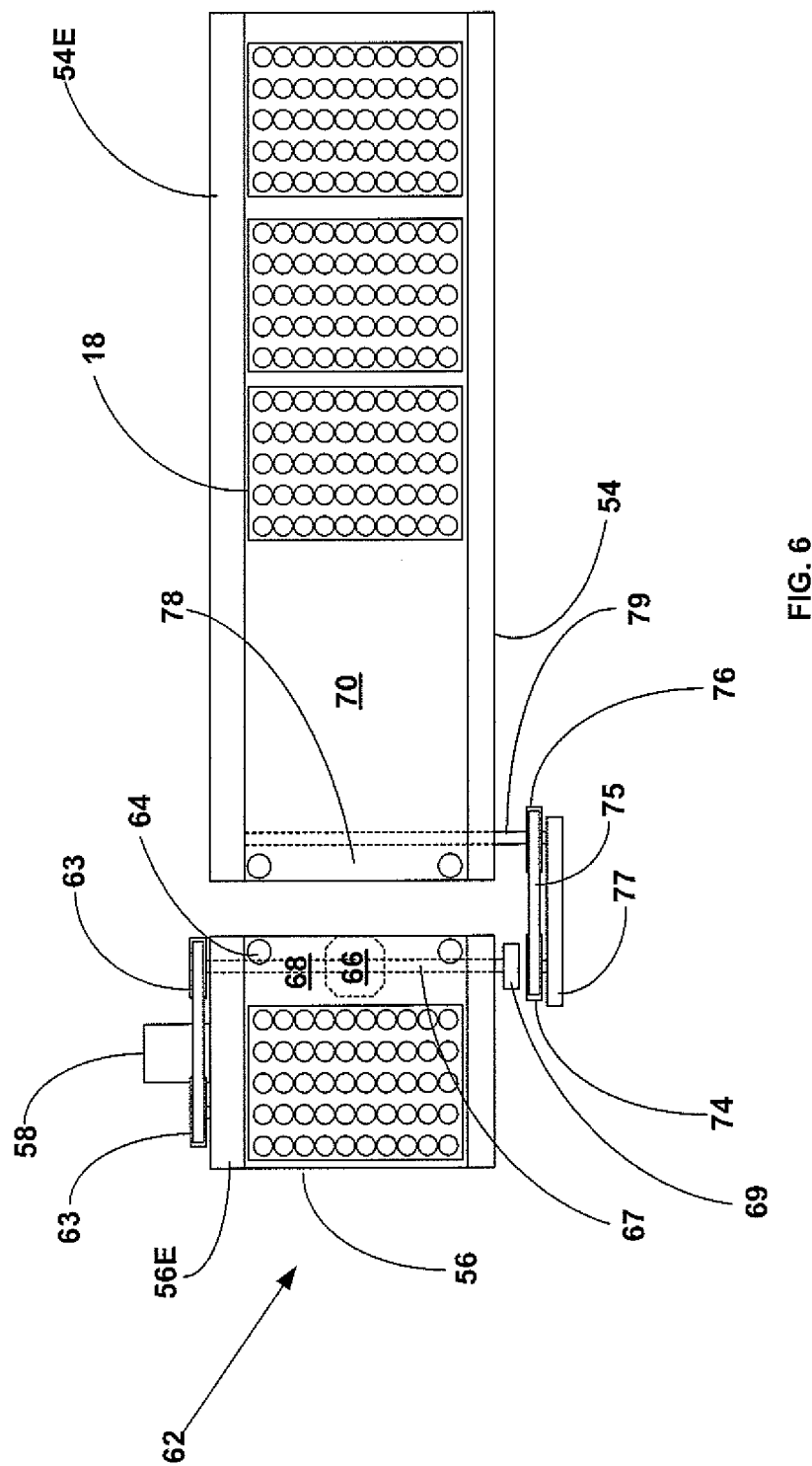
FIG. 6 is a plan view of the enlarged sectional view of a portion of the sample storage and retrieval unit of FIG. 5 illustrating a conveyor drive system.

Another important feature of the present invention is a motorized elevator belt or track system 62 for moving racks 18 horizontally between vertically translatable elevator 56 and shelves 54 in a random sequence. As used herein, a "random" sequence is any sequence other than the sequence at which the racks 18 were originally placed on shelves 54. In an exemplary embodiment, illustrated in the expanded side elevation section view of FIG. 5, elevator belt or track system 62 comprises vertically translatable elevator 56 equipped with retractable stop gates 64 at the edge of elevator 56 proximate shelf 54 that is extended upwardly when a rack 18 is carried thereon and that is retracted downwardly when a rack 18 is to be moved onto a shelf 54, as explained hereinafter. Elevator 56 is equipped with a fixed stop gate 57 at the left side of elevator 56 in order to secure a rack 18 moved thereon in a rack loading process described hereinafter. An important feature of storage and retrieval unit 50 is a coupled conveyor system 65 adapted for removing a rack 18 from elevator 56 and placing the rack 18 on a shelf 54 and vice-versa. To accomplish this rack movement of 18, elevator 56 is equipped (between its top and bottom surfaces) with a bi-directional motor 66 having a shaft 67 that engages and drives an elevator belt conveyor 68 (along the top surface of elevator 56) at a first speed in either a clockwise or counter-clockwise direction Somewhat similarly, shelves 54 are equipped with a shelf belt conveyor 70 that can be freely driven in both clockwise and counter-clockwise directions on supporting bearings 72 and also have retractable stop gates 64 at the edge of shelf 54 proximate elevator 56 that are extended when a rack 18 is carried thereon and that are retracted when a rack 18 is to be moved onto elevator 56, as explained hereinafter. As seen in FIG. 6, a top view within storage and retrieval unit 50 of elevator 56 and shelf 54 illustrating how the central portion of their upper surfaces is recessed enabling elevator belt conveyor 68 and shelf belt conveyor 70 to be driven along their respective upper surfaces between raised edges 56E and 54E respectively, to thereby horizontally translate a rack 18 in either leftwards or rightwards directions between raised edges 56E and 54E, respectively.

Another important feature of elevator belt or track system 62, also seen in FIG. 6, is a selectably engageable drive system configured to couple the powered elevator belt conveyor 68 with the non-powdered shelf belt conveyor 70 when elevator 56 is aligned with a shelf 54. When the elevator belt conveyor 68 and shelf belt conveyor 70 are coupled together, bidirectional motor 66 can drive both elevator belt conveyor 68 and shelf belt conveyor 70 in the same right-to-left or left-to-right direction To effect separation of a rack 18 on elevator 56 from a rack 18 on the shelf 54, the drive ratios of the elevator belt conveyor 68 and shelf belt conveyor 70 are selected so that the elevator belt conveyor 68 is driven at a higher speed relative to the speed of the shelf belt conveyor 70 even though both are powered by the single motor 66. As a rack 18 is moved onto the elevator belt conveyor 68 from the shelf belt conveyor 70, the difference in drive speed between the two conveyors 68 and 70 will cause rack 18 to move onto the elevator 56 at a higher speed compared to racks 18 on shelf 54 that are moving at a slower speed. This difference in speeds between conveyors 68 and 70 generates a gap between a rack 18 being loaded onto elevator 56 and those racks 18 remaining on shelf 54. Once rack 18 is fully moved onto elevator 56 by elevator belt conveyor 68, bi-directional motor 66 is stopped, stop gates 64 are raised and the elevator belt conveyor 68 is decoupled from the from the shelf belt conveyor 70. Elevator 56 is free to move rack 18 carried thereon up or down to another shelf 54.

FIG. 6 further illustrates a pair of sprockets attached to shelf 54 on a sprocket arm 77 affixed to shelf 54 by a bracket (not illustrated), a first toothed sprocket 74 and a second toothed sprocket 76 coupled by a chain 75, forming the drive system for the shelf belt conveyor 70. First toothed sprocket 74 is mounted proximate the end of a rotating shaft 67 of motor 66 when the elevator belt conveyor 68 is aligned with the shelf belt conveyor 70. A coupling clutch 69 is mounted on the end of rotating shaft 67, thereby proximate first toothed sprocket 74 so that first toothed sprocket 74 can freely rotate when clutch 69 is disengaged. When coupling clutch 69 is engaged, first toothed sprocket 74 can be rotated clockwise or counter-clockwise when motor 66 is activated. Second toothed sprocket 76 is affixed to an end of a rotating shaft 79 that engages shelf belt conveyor 70 so that as second toothed sprocket 76 is driven in a clockwise direction by a clockwise rotation of first toothed sprocket 74, shelf belt conveyor 70 is driven from left to right and vice versa. To one skilled in that art, it is evident that bi-directional motor 68, in conjunction with engagable coupling clutch 69, is operable to cause elevator belt conveyor 68 and shelf belt conveyor 70 to be driven along their respective upper surfaces between raised edges 56E and 54E, respectively, in both right-to-left and left-to-right directions. At the same time, it is evident that when clutch 69 is disengaged, first toothed sprocket 74 is no longer coupled to the shelf drive system (when it is desired to move elevator 56 vertically into alignment with another shelf 54 and/or into alignment with loading tray 60). As explained previously, it is advantageous that the tooth ratio between first toothed sprocket 74 and second toothed sprocket 76 be selected such that when bi-directional motor 66 rotates shaft 67 and drives elevator belt conveyor 68 at a first speed and, when first toothed sprocket 74 and second toothed sprocket 76 are engaged together via chain 70, second toothed sprocket 76 rotates shaft 78 and thereby drives belt conveyor 70 at a second speed, the second speed being slightly lower than the first speed at which elevator belt conveyor 68 is moving.

Figure 6A:
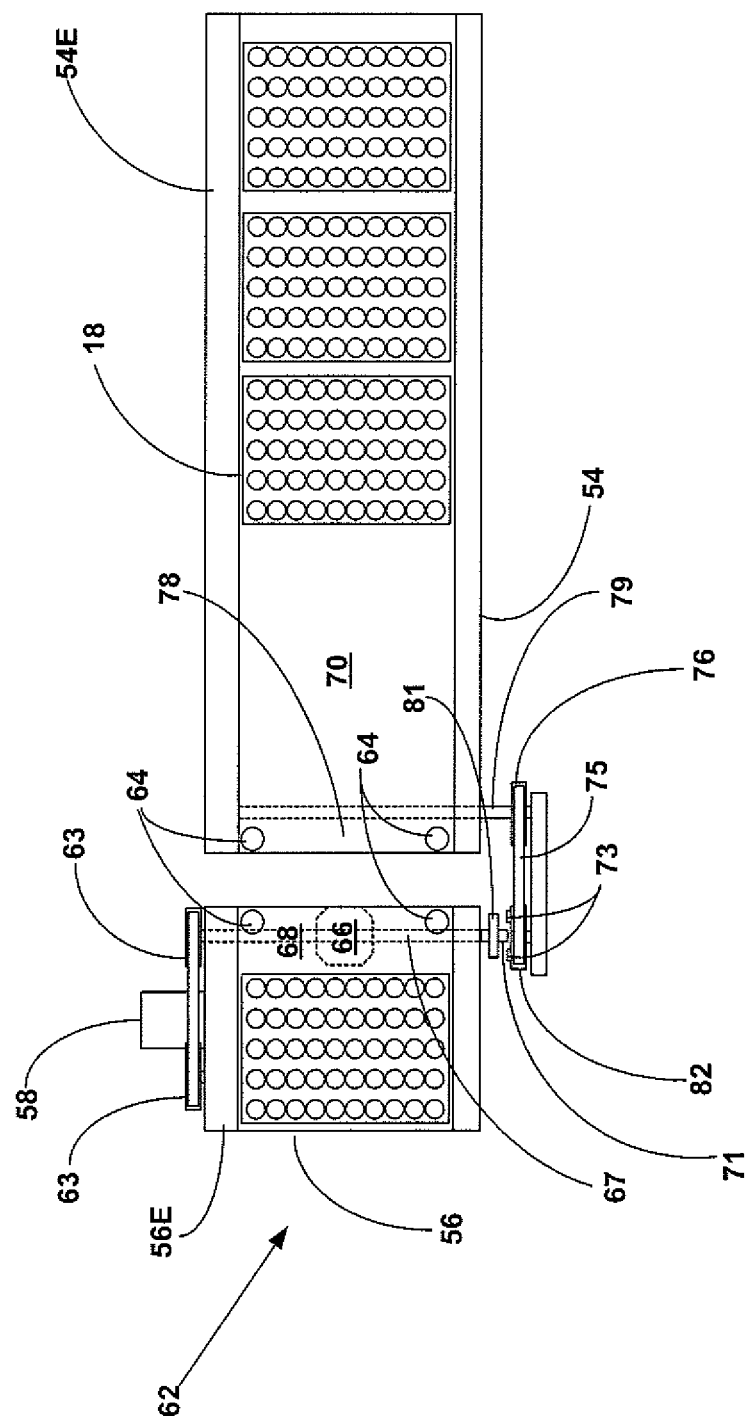
FIG. 6A is a plan view of the enlarged sectional view of a portion of the sample storage and retrieval unit of FIG. 5 illustrating an alternate conveyor drive system.
Figure 7:
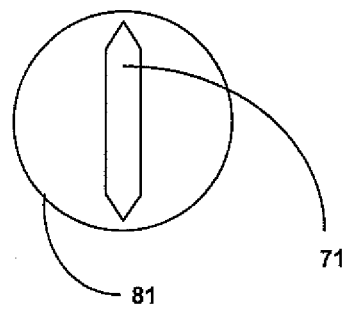
FIG. 7 is a side elevation view of a rotatable elevator disk portion of an alternate conveyor drive system.
Figure 8:
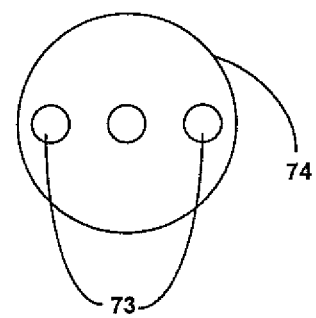
FIG. 8 is a side elevation view of a rotatable shelf disk portion of an alternate conveyor drive system.
Figure 7A:
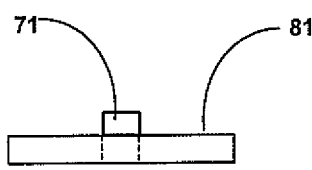
FIG. 7A is a top plan view of the rotatable elevator disk portion of the alternate conveyor drive system of FIG. 7.
Figure 8A:
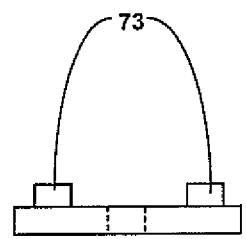
FIG. 8A is a top plan view of the rotatable shelf disk portion of the alternate conveyor drive system of FIG. 7.
Figure 9:
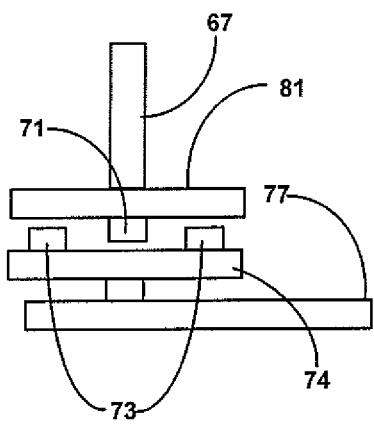
FIG. 9 illustrates the rotatable elevator disk portion of FIG. 7 intersecting the shelf disk portion of FIG. 8.
Figure 10:
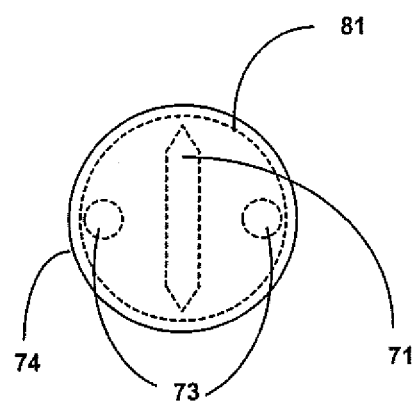
FIGS. 10-10A-10B illustrate the elevator disk portion of FIG. 7 being vertically moveable relative to the rotatable shelf disk portion of FIG. 8.
Figure 10A:
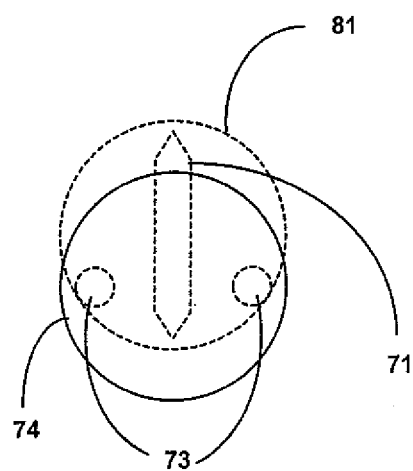
Figure 10B:
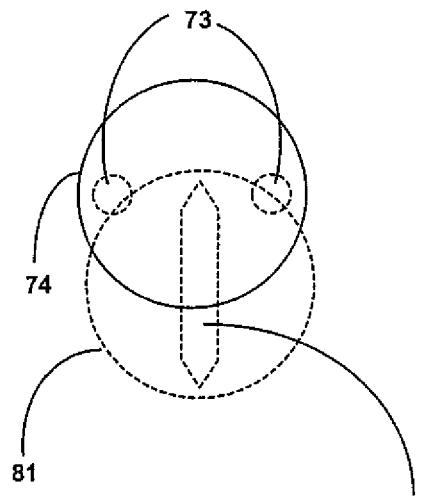
Figure 11:
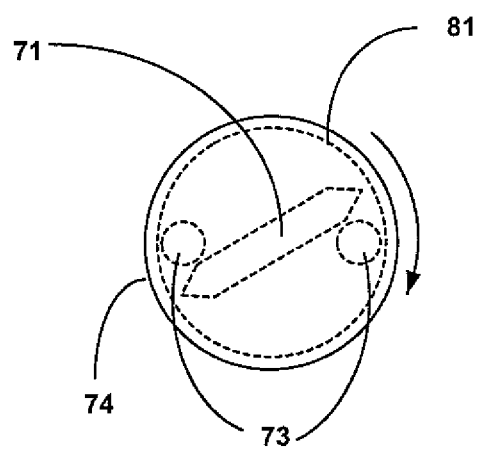
FIGS. 11-11A illustrate the elevator disk portion of FIG. 7 engaged with and rotating the rotatable shelf disk portion of FIG. 8.
Figure 11A:
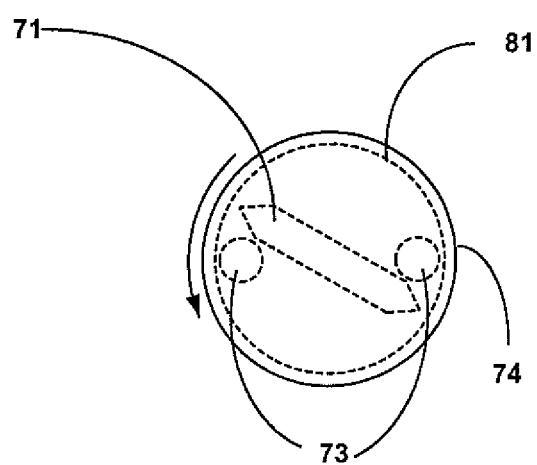

In an alternate selectably engageable drive system for coupling powered elevator belt conveyor 68 with non-powdered shelf belt conveyor 70 so that elevator 56 can be selectably engaged with drive shelf 54, as illustrated in FIG. 6A, coupling clutch 69 and first toothed sprocket 74 can be replaced by a rotatable disk 81 attached to shaft 67 and another rotatable disk 82 mounted to disk arm 77 and engaged to second toothed sprocket 76 by chain 75. Rotatable disk 81 has a single projecting fin 71 mounted to the face proximate rotatable disk 82 (see FIGS. 7 and 7A) and rotatable disk 82 has a pair of projecting pins 73 mounted to the face proximate rotatable disk 81 (see FIGS. 8 and 8A). FIG. 9, taken with FIG. 10, shows the intersection of rotatable disk 81 attached to shaft 67 and rotatable disk 82 mounted to disk arm 77 whereby fin 71 may be freely moved vertically between pins 73 when rotatable disk 81 is in an orientation that orients fin 81 in a generally vertical direction, as illustrated in FIGS. 10A and 10B. When it is desired to drive shelf belt conveyor 70 from left to right, disk 81 is driven by motor 66 in a clockwise direction (see FIG. 11) causing fin 71 to engage pins 73, thereby rotating disk 74 in a clockwise direction. Second toothed sprocket 76 will likewise be rotated clockwise by means of chain 75. Reversing the direction of rotation of motor 66 will similarly cause shelf belt conveyor 70 to be driven from right to left.

Figure 12:
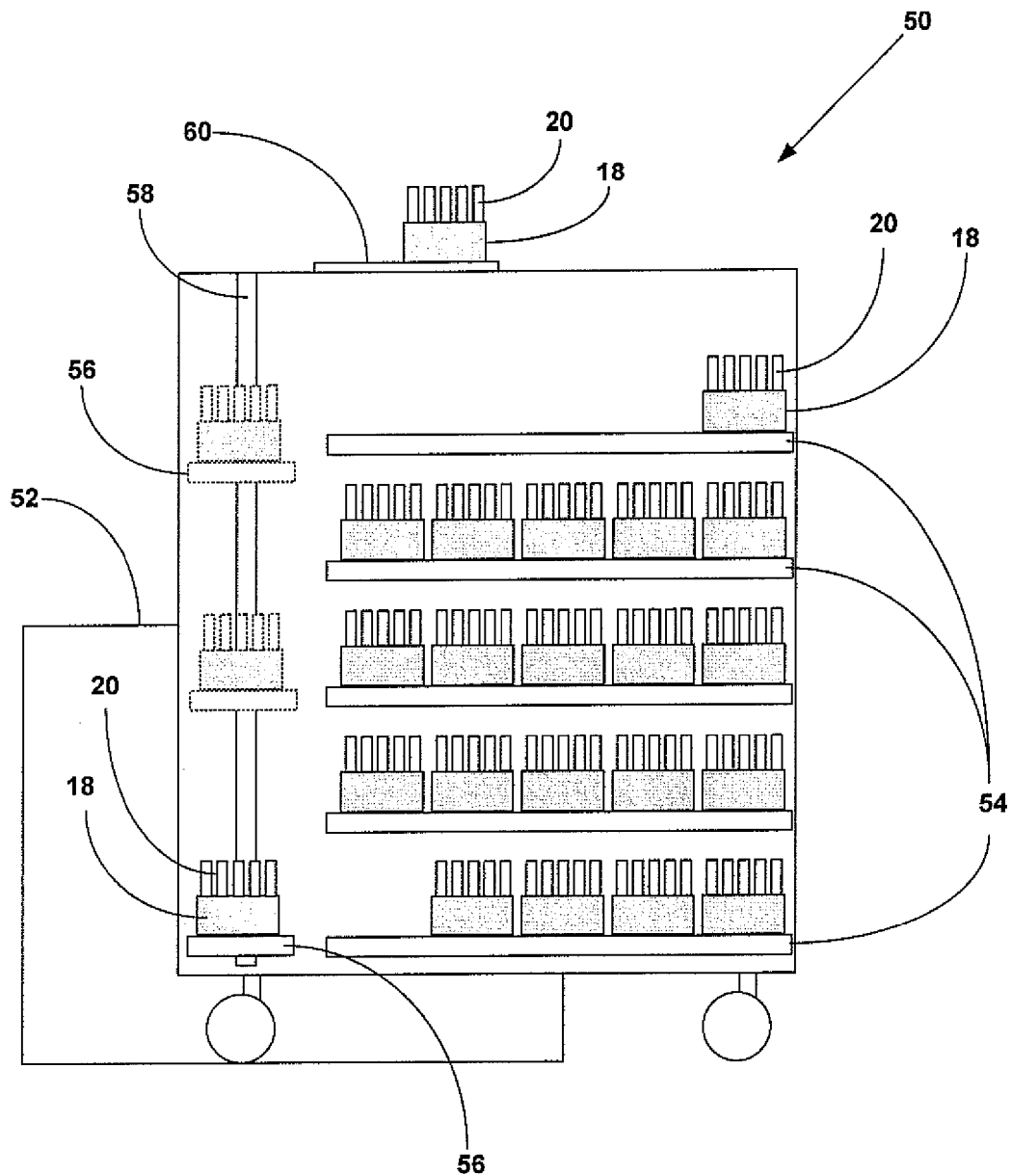
FIG. 12 is a sectional side elevation view of the sample storage and retrieval unit of the present invention illustrating how racks are moved between shelves by the vertically translatable elevator.

FIG. 12 further illustrates how racks 18 are moved between shelves 54 by elevator 56, in particular rack 18 being moved from the lowermost shelf 54 of FIG. 2 to the uppermost shelf 54 of FIG. 12. For purposes of illustration, rack 18 is shown in dashed lines as it "progress" from the lowermost shelf 54 onto uppermost shelf 54. First, clutch 69 is disengaged so that first toothed sprocket 74 is freely rotatable and elevator 56 is therefore disengaged from lowermost shelf 54. Next, motorized belt or track 58 is activated as to vertically move elevator 56 from a position horizontally aligned with the lowermost shelf 54, to a position horizontally aligned with uppermost shelf 54. It should be noted that as elevator 56 is moved vertically, clutch 69 remains disengaged so that elevator 56 is therefore disengaged from all first toothed sprockets 74 affixed to shelves 54 between the lowermost shelf 54 of FIG. 2 to the uppermost shelf 54 of FIG. 12. However, when elevator 56 is horizontally aligned with the uppermost shelf 54 of FIG. 12, clutch 69 is activated so as to engage first toothed sprocket 74 and thereby also engage second toothed sprocket 76 affixed to uppermost shelf 54. At this point, retractable stop gates 64 at the "right" edge of elevator 56 and at the open end of shelf 54 are retracted, motor 66 is activated to rotate first toothed sprocket 74 "clockwise" thereby moving elevator belt conveyor 68 and shelf belt conveyor 70 between raised edges 56E and 54E, respectively, in a left-to-right direction and transferring rack 18 from elevator 56 onto lowermost shelf 54. As indicated by the right-pointing arrow in FIG. 12, motor 66 continues to be activated thereby moving rack 18 along shelf belt conveyor 70 until it is stopped against another rack 18 already stored at the right end of shelf 54. During this process, rack 18 already stored at the right end of shelf 54, "rides over" moving shelf belt conveyor 70.

Figure 13:
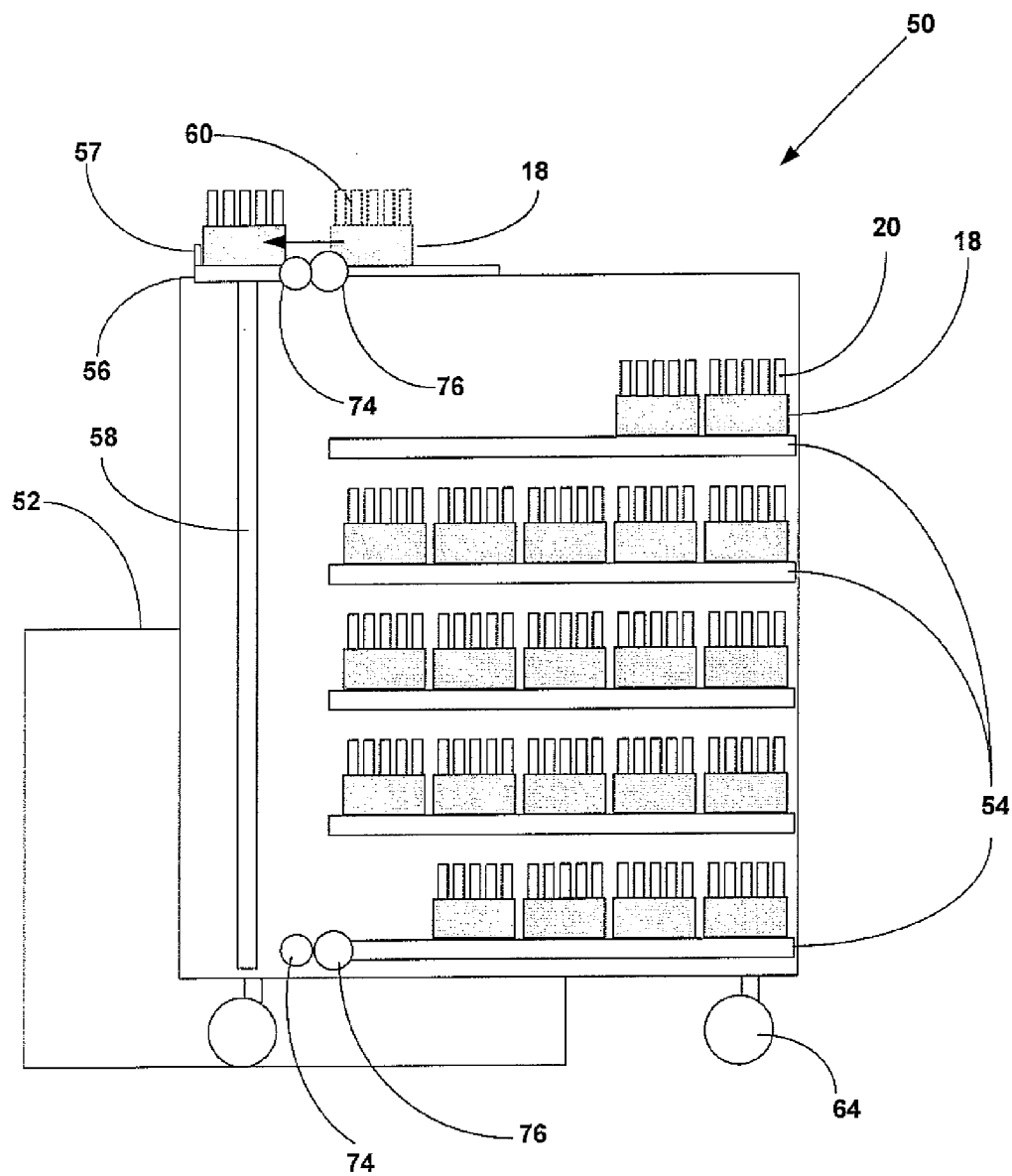
FIG. 13 is a sectional side elevation view of the sample storage and retrieval unit of the present invention illustrating how a rack is removed from a loading tray by the vertically translatable elevator.

FIG. 13 illustrates another important feature of storage and retrieval unit 50 wherein a rack 18 placed atop loading tray 60 is to be stored on a shelf 54 therein in a process somewhat like the reversed of FIG. 12. First, clutch 69 is disengaged so that first toothed sprocket 74 is freely disengaged from second toothed sprocket 76 affixed to uppermost shelf 54. Next, motorized belt or track 58 is activated as to vertically move elevator 56 through opening 62 to a position horizontally aligned with loading tray 60. Clutch 69 is activated so that first toothed sprocket 74 engages second toothed sprocket 76 affixed to loading tray 60 and retractable stop gates 64 at the "right" edge of elevator 56 and at the left end of loading tray 60 are retracted. Motor 66 is then activated to rotate first toothed sprocket 74 "counter-clockwise" thereby moving elevator belt conveyor 68 and loading tray conveyor 61 in a right-to-left direction and transferring rack 18 from loading tray onto elevator 56. As indicated by the left-pointing arrow in FIG. 13, motor 66 continues to be activated thereby moving rack 18 along loading tray conveyor 61 until it is stopped against stop gate 57 at the left side of elevator 56. Retractable stop gates 64 at the "right" edge of elevator 56 are activated so as to securely retain rack 18 on elevator 56 while elevator 56 is lowered into storage and retrieval unit 50 and rack 18 is placed upon a shelf 54 therein. In a similar rack transferring process, any rack 18 on a shelf 54 within storage and retrieval unit 50 can be moved from a shelf 54 onto elevator 56 by the combination of motorized belt or track 58, clutch 69, first toothed sprocket 74, second toothed sprocket 76, retractable stop gates 64 and motor 66.

Importantly, during the transferring step, because the tooth ratio between first toothed sprocket 74 and second toothed sprocket 76 is selected such that motor 66 drives elevator belt conveyor 68 at a first speed and loading tray conveyor 70 at a second speed, the second speed being slightly lower than the first speed at which elevator belt conveyor 68 is moving, then rack 18 is more rapidly "pulled" onto elevator 56 that rack 18 is moved along loading tray conveyor 61 thereby creating an "open gap". This gap allows room for stop gates 64 to raise and prevent a rack 18 from falling off shelf 54 or elevator 56 when mobile storage and retrieval unit 50 is in transit.

From the above description, it is clear that the elevator belt or track system 62 of storage and retrieval unit 50 has a number of features that provide the ability to move a rack 18 from loading tray 60 onto any of a number of shelves 54 as well as to move racks 18 between shelves 54 and/or onto loading tray 60. It is also clear that because racks 18 are loaded onto shelves 54 in a "last-in-first-out" order, it is necessary to reserve some empty space on at least one shelf 54 so that racks 18 may be "shuffled" between racks 54 in order to be able to randomly access any particular rack 18 of interest. All of these operations may be controlled and tracked by a conventional computer 17, preferably a microprocessor based central processing unit CPU 17 housed as part of or separate from storage and retrieval unit 50, and having software, firmware, or hardware commands or circuits typical of those skilled in the art of computer-based electromechanical control programming. Such a CPU 17 would also receive signals from a number of sensors, including bar-code readers 19 strategically located throughout storage and retrieval unit 50 to track and confirm the locations of racks 18 within storage and retrieval unit 50 from the time racks 18 are originally stored on shelves 54, shuffled between shelves 54 and/or removed from within storage and retrieval unit 50. In addition, CPU 17 would advantageously be linked, directly or by a wireless router 13 to computer 15 of LAS 10 so that whenever and if a sample tube 20 retaining sample on which it was desired to conduct a re-testing was retained within storage and retrieval unit 50, appropriate commands from computer 15 would cause CPU 17 housed of storage and retrieval unit 50 to retrieve the rack 18 carrying tube 20 from a shelf 54 and to place rack 18 upon loading tray 60.

Figure 14:
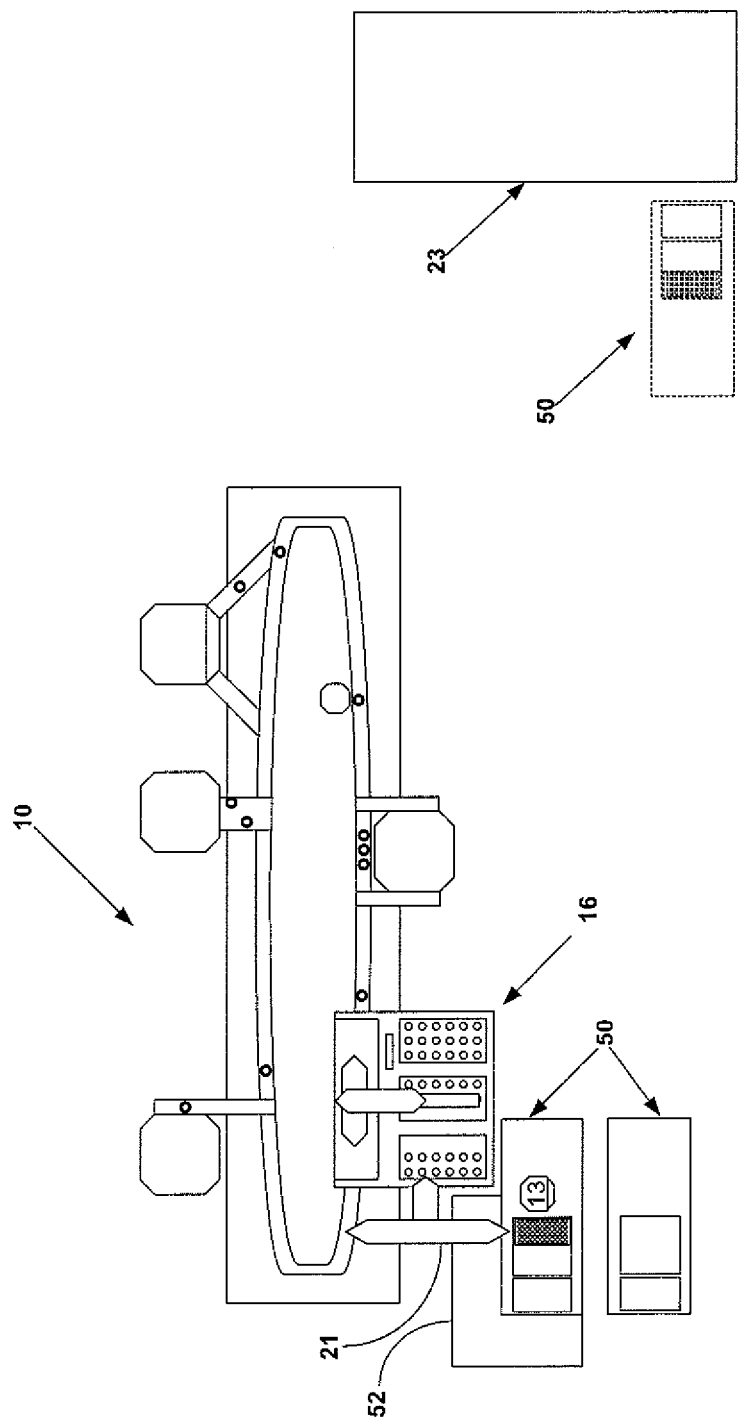
FIG. 14 is a simplified schematic plan view of an automated sample handling system of FIG. 1 illustrating interaction with the sample storage and retrieval unit of the present invention; and, FIG. 15 is an alternate embodiment of the sample storage and retrieval unit of the present invention.

As schematically illustrated in FIG. 14, storage and retrieval unit 50 is advantageously placed nearby LAS 10 whereby rack 18 could then be automatically moved using a robotic like device 21 to replace rack 18 into sample tube loading/unloading station 16 and be re-processed as described above. Alternately, sample tube loading/unloading station 16 may be equipped to move racks to and from loading tray 60 of storage and retrieval unit 50. FIG. 14 illustrates the use of a first storage and retrieval unit 50 shown as docked into stationary refrigeration unit 52 and in the process of being loaded with racks 18. A second storage and retrieval unit 50 is located nearby so that when the first storage and retrieval unit 50 is filled with racks, the first storage and retrieval unit 50 can be undocked from stationary refrigeration unit 52 and wheeled by an operator to a distantly located, conventional large volume sample storage refrigerator 23 where racks 18 within first storage and retrieval unit 50 (shown in dotted lines) are automatically removed from shelves 54 using elevator 56 and placed within shelving structures inside sample storage refrigerator 22. During this unloading process, the identity of each sample rack 18 would typically be confirmed by a machine indicia reading scanner and provided to the LAS and/or a hospital's LIS by wireless router 13. To facilitate such operations, storage and retrieval unit 50 would be equipped with a conventional re-chargeable battery power source 25, like seen in FIG. 2.

Figure 15:
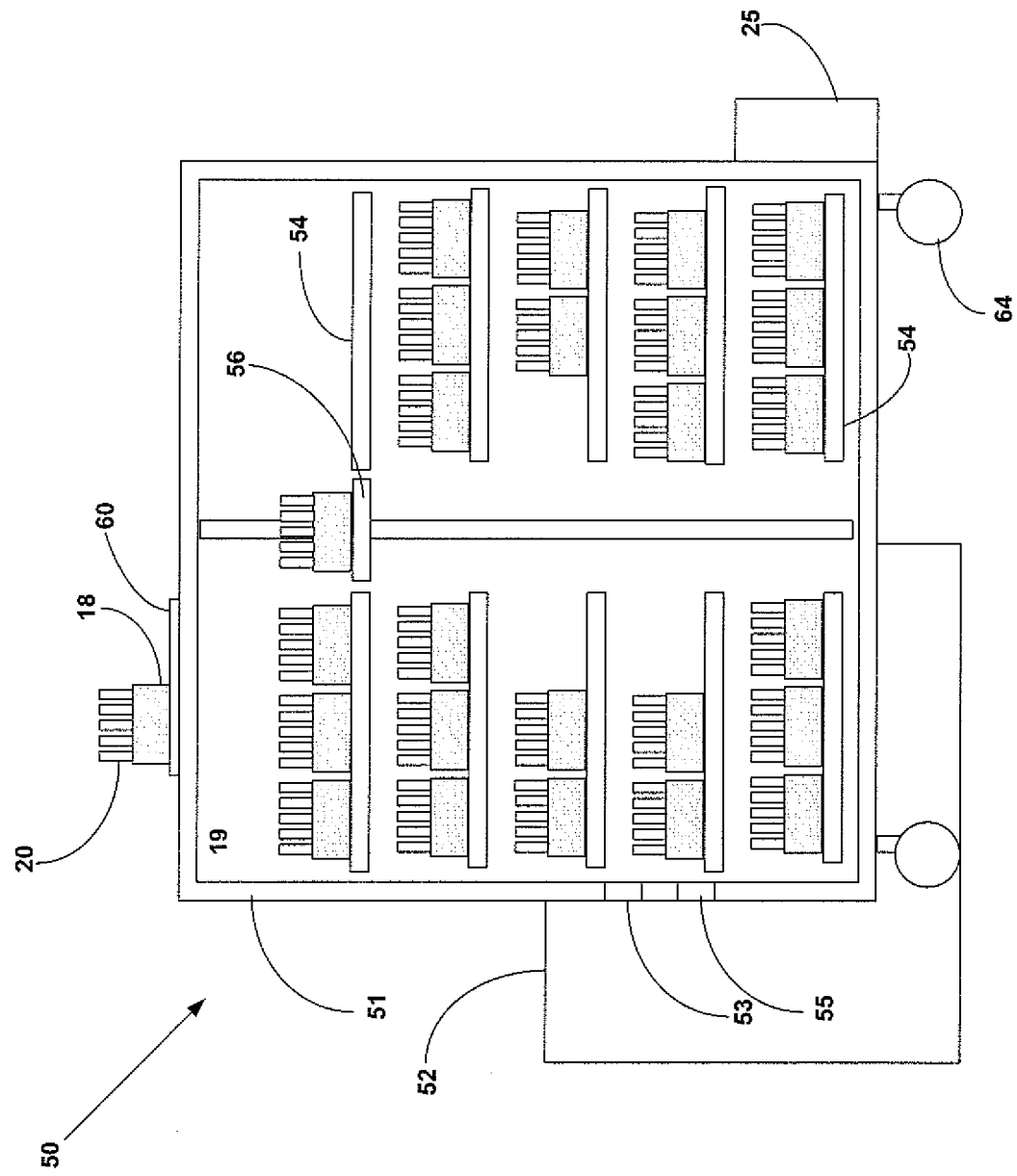

FIG. 15 is an alternate embodiment of the storage and retrieval unit 50 of the present invention wherein elevator 56 is located between two columns of shelves 54 so as to decrease the time required to access and rack 18 stored on a shelf 54.

Those skilled in the art will appreciate that the embodiments of the invention disclosed herein are illustrative of the principles of the invention and that other modifications may be employed which are still within the scope of the invention. For example, obvious variants of the invention would include alternate drive systems for the elevator and shelf conveyor, different selective coupling means between the two drive systems, a chain-like belt in place of the conveyor belts, racks adapted to contain items other than patient samples.

What is claimed is:

1. A mobile storage and retrieval unit for housing a number of sample racks, the storage and retrieval unit comprising:
   a housing having an interior and an exterior top surface;
   a number of interior shelves disposed in the interior, each interior shelf capable of holding at least one of the sample racks;
   a loading tray supporting one of the sample racks on the exterior top surface;
   a vertically translatable elevator capable of holding one of the racks thereon and capable of moving between positions aligned with each of the interior shelves to a position aligned with the loading tray;
   a conveyor system adapted to move one of the racks from the elevator onto one of the interior shelves; and
   at least one duct adapted to convey refrigerated air into the housing interior.

2. The mobile storage and retrieval unit of claim 1, wherein the conveyor system is further adapted for moving one of the racks from one of the shelves onto the elevator.

3. The mobile storage and retrieval unit of claim 1, wherein the conveyor system is further adapted for moving one of the racks between the loading tray and the elevator.

4. The mobile storage and retrieval unit of claim 1, wherein the at least one duct is connected to a source of refrigerated air.

5. The storage and retrieval unit of claim 1 wherein the conveyor system comprises a clutch mounted to a motor on the elevator and first and second sprockets attached to the shelves, the clutch and sprockets being engageable together when the elevator is horizontally aligned with one of the shelves.

6. The storage and retrieval unit of claim 5 wherein the sprocket ratio between the first sprocket and second sprocket is selected such that the motor drives the first sprocket at a first speed and the second sprocket at a second speed, the second speed being lower than the first speed.

7. The mobile storage and retrieval unit of claim 1, wherein the conveyor system comprises a rotatable fin mounted to a motor on the vertically translatable elevator, and a rotatable disk with protruding pins attached to the shelves, the rotatable fin and protruding pins being engageable together when the elevator is horizontally aligned with one of the shelves.

8. The mobile storage and retrieval unit of claim 1, wherein the housing further comprises thermally insulated exterior walls.

9. The mobile storage and retrieval unit of claim 1, further comprising sensors for tracking the location of racks stored therein.

10. The mobile storage and retrieval unit of claim 1, further comprising sensors for detecting the identification of racks stored therein.

11. The mobile storage and retrieval unit of claim 1, further comprising a central processing unit programmed to control the vertically translatable elevator and conveyor system so as to retrieve any of the racks from any of the shelves and to place one of the racks upon the loading tray.

12. The mobile storage and retrieval unit of claim 1, wherein the interior shelves are disposed in two columns and the vertically translatable elevator is disposed centrally between the columns.

13. The mobile storage and retrieval unit of claim 1, wherein the vertically translatable elevator and conveyor system are battery powered.

14. The mobile storage and retrieval unit of claim 1, wherein the sample racks are capable of holding patient samples, reagents, calibration liquids, and/or Quality Control solutions.

15. The mobile storage and retrieval unit of claim 1, further comprising a mechanism adapted to assist in the movement of the unit attached to a surface of the mobile storage and retrieval unit.

16. The mobile storage and retrieval unit of claim 1, wherein the loading tray further comprises:
- a loading tray conveyor that can be freely driven in both clockwise and counter-clockwise directions; and
- a shelf belt conveyor that can be freely driven in both clockwise and counter-clockwise directions.

* * * * *